(12) United States Patent
Serhal et al.

(10) Patent No.: US 10,538,465 B2
(45) Date of Patent: Jan. 21, 2020

(54) COMPLEX COMPRISING ODH UNIT WITH INTEGRATED OXYGEN SEPARATION MODULE

(71) Applicant: NOVA Chemicals (International) S.A., Fribourg (CH)

(72) Inventors: Kamal Serhal, Calgary (CA); Vasily Simanzhenkov, Calgary (CA); Shahin Goodarznia, Calgary (CA); David Gent, Red Deer (CA); Mark Williamson, Red Deer County (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 16/406,355

(22) Filed: May 8, 2019

(65) Prior Publication Data
US 2019/0263734 A1  Aug. 29, 2019

Related U.S. Application Data

(62) Division of application No. 15/933,960, filed on Mar. 23, 2018.

(30) Foreign Application Priority Data

Apr. 25, 2017  (CA) .................... 2965062

(51) Int. Cl.
*C07C 5/327* (2006.01)
*C07C 5/32* (2006.01)
(Continued)

(52) U.S. Cl.
CPC .......... *C07C 5/322* (2013.01); *B01D 53/1475* (2013.01); *B01D 53/22* (2013.01);
(Continued)

(58) Field of Classification Search
CPC ....... C07C 5/327; C07C 5/3332; C07C 7/005; C07C 7/04; C07C 7/144
(Continued)

(56) References Cited

U.S. PATENT DOCUMENTS 3,420,911 A  1/1969 Woskow et al.
3,420,912 A  1/1969 Woskow et al.
(Continued)

FOREIGN PATENT DOCUMENTS

EP  0 261 264 A1  3/1988

OTHER PUBLICATIONS

Peri, J.B. and Hensley, A. L., Jr; The Surface Structure of Silica Gel; The Journal of Physical Chemistry, vol. 72, No. 8, Aug. 1968; pp. 2926-2933.

*Primary Examiner* — Thuan D Dang
(74) *Attorney, Agent, or Firm* — Lawrence T. Kale; Thomas J. Styslinger

(57) ABSTRACT

Oxidative dehydrogenation is an alternative to the energy extensive steam cracking process presently used for the production of olefins from paraffins, but has not been implemented commercially partially due to the unstable nature of hydrocarbon/oxygen mixtures, and partially due to the cost involved in the construction of new facilities. An oxidative dehydrogenation chemical complex designed to reduce costs by including integration of an oxygen separation module that also addresses safety concerns and reduces emission of greenhouse gases is described.

15 Claims, 3 Drawing Sheets

(51) Int. Cl.
*C07C 9/06* (2006.01)
*C07C 11/04* (2006.01)
*B01J 23/887* (2006.01)
*C07B 35/04* (2006.01)
*B01D 53/22* (2006.01)
*C07C 5/48* (2006.01)
*B01D 53/14* (2006.01)
*B01D 53/75* (2006.01)
*B01J 23/652* (2006.01)
*B01J 23/00* (2006.01)
*B01J 8/24* (2006.01)
*B01J 23/22* (2006.01)
*B01J 23/28* (2006.01)
*B01J 8/02* (2006.01)

(52) U.S. Cl.
CPC .............. *B01D 53/75* (2013.01); *B01J 23/00* (2013.01); *B01J 23/6525* (2013.01); *B01J 23/8877* (2013.01); *C07B 35/04* (2013.01); *C07C 5/48* (2013.01); *C07C 9/06* (2013.01); *C07C 11/04* (2013.01); *B01D 2252/204* (2013.01); *B01D 2256/24* (2013.01); *B01D 2257/104* (2013.01); *B01J 8/02* (2013.01); *B01J 8/24* (2013.01); *B01J 23/22* (2013.01); *B01J 23/28* (2013.01); *C07C 2523/847* (2013.01); *C07C 2523/887* (2013.01)

(58) Field of Classification Search
USPC .................................. 585/655, 658, 818, 862
See application file for complete search history.

(56) References Cited

U.S. PATENT DOCUMENTS

| | | |
|---|---|---|
| 3,904,703 A | 9/1975 | Lo et al. |
| 4,250,346 A | 2/1981 | Young et al. |
| 4,450,313 A | 5/1984 | Eastman et al. |
| 4,524,236 A | 6/1985 | McCain |
| 4,596,787 A | 6/1986 | Manyik et al. |
| 4,899,003 A | 2/1990 | Manyik et al. |
| 5,202,517 A | 4/1993 | Minet et al. |
| 6,518,476 B1 * | 2/2003 | Culp ................. C07C 2/84 585/655 |
| 6,521,808 B1 | 2/2003 | Ozkan et al. |
| 6,566,573 B1 | 5/2003 | Bharadwaj et al. |
| 6,624,116 B1 | 9/2003 | Bharadwaj et al. |
| 6,891,075 B2 | 5/2005 | Liu |
| 7,319,179 B2 | 1/2008 | Lopez Nieto et al. |
| 9,545,610 B2 | 1/2017 | Simanzhenkov et al. |
| 2011/0245571 A1 | 10/2011 | Kustov et al. |

\* cited by examiner

COMPLEX COMPRISING ODH UNIT WITH INTEGRATED OXYGEN SEPARATION MODULE

CROSS REFERENCE TO RELATED PATENT APPLICATION

This application is a divisional of U.S. application Ser. No. 15/933,960, filed on Mar. 23, 2018, entitled "Complex Comprising ODH Unit With Integrated Oxygen Separation Module", which is herein incorporated by reference in its entirety.

FIELD OF THIS DISCLOSURE

The present disclosure relates generally to oxidative dehydrogenation (ODH) of lower alkanes into corresponding alkenes. More specifically, the present disclosure relates to a chemical complex for ODH that includes an oxygen separation module.

BACKGROUND

Catalytic oxidative dehydrogenation of alkanes into corresponding alkenes is an alternative to steam cracking. The latter is the method of choice for the majority of today's commercial scale producers. Despite its widespread use, steam cracking has its downsides.

First, steam cracking is energy intensive, requiring temperatures in the range of 700° C. to 1000° C. to satisfy the highly endothermic nature of the cracking reactions.

Second, the process is expensive owing to the high fuel demand, the requirement for reactor materials that can withstand the high temperatures, and the necessity for separation of unwanted by-products using downstream separation units.

Third, the production of coke by-product requires periodic shutdown for cleaning and maintenance.

Finally, for ethylene producers, the selectivity for ethylene is only around 80 to 85% for a conversion rate that doesn't generally exceed 60%. In contrast, ODH operates at lower temperature, does not produce coke, and using newer developed catalysts provides selectivity for ethylene of around 98% at close to 60% conversion. The advantages of ODH are, however, overshadowed by the requirement for the potentially catastrophic mixing of oxygen with a hydrocarbon.

The concept of ODH has been known since at least the late 1960's. Since that time, considerable effort has been expended on improving the process, including improving catalyst efficiency and selectivity. This has resulted in numerous patents for various catalyst types including carbon molecular sieves, metal phosphates, and most notably mixed metal oxides. Early catalyst U.S. patents assigned to Petro-Tex Chemicals, including U.S. Pat. Nos. 3,420,911 and 3,420,912 in the names of Woskow et al., taught the use of ferrites in the oxidative dehydrogenation of organic compounds. The ferrites are introduced into a dehydrogenation zone containing the organic compound and an oxidant for a short period, then to a regeneration zone for reoxidation, and then fed back to the dehydrogenation zone for another cycle.

U.S. Pat. No. 4,450,313, issued May 22, 1984 to Eastman et al., assigned to Phillips Petroleum Company, discloses a catalyst of the composition $Li_2O$—$TiO_2$, which is characterized by a low ethane conversion not exceeding 10%, in spite of a rather high selectivity to ethylene (92%), using a process where temperature is at or higher than 650° C.

The preparation of a supported catalyst useful for low-temperature oxidative dehydrogenation of ethane to ethylene is disclosed in U.S. Pat. No. 4,596,787, issued Jun. 24, 1986 to Manyik et al., assigned to Union Carbide Corporation. A supported catalyst for the low-temperature gas-phase oxidative dehydrogenation of ethane to ethylene is prepared by (a) preparing a precursor solution having soluble and insoluble portions of metal compounds, (b) separating the soluble portion, (c) impregnating a catalyst support with the soluble portion and (d) activating the impregnated support to obtain the catalyst. The calcined catalyst has the composition

$$Mo_aV_bNb_cSb_dX_e$$

wherein X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5-0.9; b is 0.1-0.4; c is 0.001-0.2; d is 0.001-0.1; and e is 0.001-0.1 when X is an element.

Other examples of low temperature oxidative dehydrogenation of ethane to ethylene using a calcined oxide catalyst containing molybdenum, vanadium, niobium and antimony are described in U.S. Pat. No. 4,524,236 A, issued Jun. 18, 1985 and U.S. Pat. No. 4,250,346 A, issued Feb. 10, 1981, both assigned to Union Carbide Corporation. The catalyst is prepared from a solution of soluble compounds and/or complexes of each of the metals. The dried catalyst is calcined by heating at 220° C. to 550° C. in air or oxygen. The catalyst precursor solutions may be supported on an inorganic oxide (e.g., silica, aluminum oxide, silicon carbide, zirconia, titania or mixtures of these). The selectivity to ethylene may be greater than 65% for a 50% conversion of ethane.

U.S. Pat. No. 4,524,236 issued Jun. 18, 1985 to McCain assigned to Union Carbide Corporation and U.S. Pat. No. 4,899,003, issued Feb. 6, 1990 to Manyik et al. assigned to Union Carbide Chemicals and Plastics Company Inc. disclose mixed metal oxide catalysts of V—Mo—Nb—Sb. At 375° C. to 400° C., the ethane conversion reached 70% with the selectivity close to 71 to 73%. However, this ethane conversion result was only achieved at very low gas hourly space velocities (i.e., 720 $h^{-1}$).

U.S. Pat. No. 6,624,116, issued Sep. 23, 2003 to Bharadwaj, et al. and U.S. Pat. No. 6,566,573 issued May 20, 2003 to Bharadwaj, et al., both assigned to Dow Global Technologies Inc., disclose Pt—Sn—Sb—Cu—Ag monolith systems that have been tested in an auto-thermal regime at T>750° C. where the starting gas mixture contains hydrogen ($H_2$:$O_2$=2:1, gas hourly space velocity (GHSV) of 180 000 $h^{-1}$). The catalyst composition is different from that of the present disclosure and the present disclosure does not contemplate the use of molecular hydrogen in the feed.

U.S. Pat. No. 6,521,808 issued Feb. 18, 2003 to Ozkan, et al, assigned to Ohio State University teaches sol gel supported catalysts for the oxidative dehydrogenation of ethane to ethylene. The catalyst appears to be a mixed metal system, such as, Ni—Co—Mo, V—Nb—Mo possibly doped with small amounts of Li, Na, K, Rb, and Cs on a mixed silica oxide/titanium oxide support. The catalyst does not provide the oxygen for the oxidative dehydrogenation, rather, gaseous oxygen is included in the feed. The patent does not teach the integration of oxygen separation from air using by-products from the ODH reaction catalyzed by the claimed catalyst.

U.S. Pat. No. 6,891,075 issued May 10, 2005 to Liu, assigned to Symyx Technologies, Inc. teaches a catalyst for the oxidative dehydrogenation of a paraffin (alkane) such as ethane. The gaseous feedstock comprises at least the alkane and oxygen, but may also include diluents (such as, argon, nitrogen, etc.) or other components (such as, water or carbon dioxide). The dehydrogenation catalyst comprises at least about 2 weight % of NiO and a broad range of other elements, preferably, Nb, Ta, and Co. The claims required a selectivity for ethylene of at least 70%, with conversions over 10%.

U.S. Pat. No. 7,319,179 issued Jan. 15, 2008 to Lopez-Nieto et al. assigned to Consejo Superior de Investigaciones Cientificas and Universidad Politecnica de Valencia discloses Mo—V—Te—Nb—O oxide catalysts that provided an ethane conversion of 50 to 70% and selectivity to ethylene up to 95% (at 38% conversion) at 360 to 400° C. The catalysts have the empirical formula $MoTe_hV_iNb_jA_kO_x$, where A is a fifth modifying element. The catalyst is a calcined mixed oxide (at least of Mo, Te, V and Nb), optionally supported on: (i) silica, alumina and/or titania, preferably silica at 20 to 70 wt. % of the total supported catalyst or (ii) silicon carbide. The supported catalyst is prepared by conventional methods of precipitation from solutions, drying the precipitate and then calcining.

There is also considerable prior art directed at the process of oxidative dehydrogenation itself, including reactor configurations and implementations for increased safety.

U.S. Pat. No. 3,904,703 issued Sep. 9, 1975 to Lo et al., assigned to El Paso Products Company, teaches a zoned or layered oxidative reactor in which following a zone for oxidative dehydrogenation there is an "oxidation zone" to oxidize the hydrogen to water. Following the oxidation zone, there is an adsorption bed to remove water from the reactants before they enter a subsequent dehydrogenation zone. This is to reduce the impact of water on downstream dehydrogenation catalysts.

EP Patent 0 261 264 B1, inventors Manyik, et. al., assigned to Union Carbide Corporation, granted Aug. 21, 1991, discloses the use of multiple reactors in series, each reactor followed by a cooling step and the addition of supplemental oxygen before each subsequent reactor. The effect of interstage cooling and addition of supplemental oxygen prior to each reactor except the final reactor is to reduce total water and acetic acid content prior to each stage.

U.S. Pat. No. 5,202,517 issued Apr. 13, 1993 to Minet et al., assigned to Medalert Incorporated, teaches a ceramic tube for use in the conventional dehydrogenation of ethane to ethylene. The "tube" is a ceramic membrane in which the ethane flows inside the tube and hydrogen diffuses out of the tube to improve the reaction kinetics. The reactive ceramic is 5 micrometers thick on a 1.5 to 2 mm thick support.

U.S. Published Application No. 20110245571 in the name of NOVA Chemicals (International) S.A. teaches oxidative dehydrogenation of ethane in a fluidized bed in contact with a bed of regenerative oxides to provide oxygen to the reactor. In this process, free oxygen is not directly mixed with the feedstock reducing the likelihood of decompositions.

U.S. Published Application No. 20180009662, filed in the name of NOVA Chemicals (International) S.A., titled "Inherently Safe Oxygen/Hydrocarbon Gas Mixer", inventor Vasily Simanzhenkov et al., discloses the use of a flooded mixer, where hydrocarbon and oxygen containing gases are mixed without fear of igniting an explosive event. This benefit is directly applicable to ODH as it provides an option for improving the safety of the process. Gases, in a ratio that falls outside of the flammability envelope, can be mixed together before introduction into an ODH reactor. This patent does not teach the incorporation of oxygen separation into the ODH process.

None of the above art teaches or suggests a chemical complex in which the by-products of the ODH process are used to drive an oxygen separation process, resulting in a relatively pure source of oxygen which can be recycled back to contribute to the ODH reaction.

In order for ODH to become a mainstream commercial option the economic benefit must outweigh the risk associated with thermal runway of the reaction. Most prior art patents are directed at improving the safety and efficiency of the reaction by developing better catalysts and systems for reducing risk. The present disclosure seeks to further improve economic efficiency by reducing the amount of costly oxygen required during steady state operations. Furthermore, the use of ODH by-products to drive oxygen separation limits the amount of carbon dioxide that would be released into the atmosphere.

SUMMARY OF DISCLOSURE

The present disclosure seeks to provide an oxidative dehydrogenation reaction complex with oxygen separation integration that is economically feasible and amenable to large scale commercial production of olefins from lower alkanes.

The present disclosure provides a chemical complex comprising, in cooperative arrangement:
(a) at least one ODH reactor, comprising an ODH catalyst, for accepting a lower alkane and oxygen, and optionally an inert diluent, and for releasing a product stream comprising unconverted lower alkane, a corresponding alkene, and possibly (optionally) carbon oxides, oxygenates, and water;
(b) a quench tower for removing oxygenates and water from said product stream;
(c) an amine wash tower for removing carbon dioxide from said product stream;
(d) a drier for removing residual water;
(e) a distillation tower for removing C2/C2+ hydrocarbons from said product stream to produce an overhead stream enriched with C1 hydrocarbons; and
(f) an oxygen separation module for accepting atmospheric air and said overhead stream to produce an oxygen enriched stream that can feed said ODH reactor.

In an embodiment of this disclosure, the chemical complex further comprises a flooded gas mixer for premixing the oxygen and the lower alkane prior to introduction into the oxidative dehydrogenation reactor.

In an embodiment of this disclosure, the chemical complex further comprises a heat exchanger immediately downstream of each at least one ODH reactor and upstream of said quench tower.

In an embodiment of this disclosure, the chemical complex further comprises a caustic wash tower immediately downstream of said amine wash.

In an embodiment, the oxidative dehydrogenation reactor uses a catalyst selected from the group consisting of:
i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1 (normalized), b=0.01 to 1.0, c=0.01 to 1.0, d=0.01 to 1.0, 0.00≤e≤0.10 and f is dependent on the oxidation state of the other elements, i.e., f is a number to satisfy the valence state of the catalyst;

ii) catalysts of the formula:

$$Ni_gA_hB_iD_jO_f$$

wherein: g is a number from 0.1 to 0.9, preferably from 0.3 to 0.9, more preferably from 0.5 to 0.85, most preferably 0.6 to 0.8; h is a number from 0.04 to 0.9; i is a number from 0 to 0.5; j is a number from 0 to 0.5; and f is a number to satisfy the valence state of the catalyst; A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is selected from the group consisting of Ca, K, Mg, Li, Na, Sr, Ba, Cs, and Rb and mixtures thereof; and O is oxygen;

iii) catalysts of the formula $$Mo_aE_kG_lO_f$$

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; and when a=1 (normalized); k is 0 to 2; l=0 to 2, with the proviso that the total value of l for Co, Ni, Fe and mixtures thereof is less than 0.5; and f is a number to satisfy the valence state of the catalyst;

iv) catalysts of the formula $$V_mMo_nNb_oTe_pMe_qO_f$$

wherein: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula $$Mo_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; and when a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

In an embodiment of this disclosure, the ODH catalyst is supported.

In an embodiment of this disclosure, the ODH reactor comprises a fixed bed reactor.

In an embodiment of this disclosure, the ODH reactor comprises a fluidized bed reactor.

In an embodiment of this disclosure, the ODH reactor comprises an outer shell and one or more internal ceramic tubes defining a separate flow passage for ethane down the interior of said tubes and an annular passage between the external shell of the reactor and the ceramic tubes defining a flow path for an oxygen containing gas.

In an embodiment of this disclosure, the ceramic tubes further comprise an internal steel mesh and an external steel mesh.

In an embodiment of this disclosure, the C2/C2+ hydrocarbons fraction leaving the distillation tower is directed to a splitter.

In an embodiment of this disclosure, the distillation tower is capable of separating the C2/C2+ hydrocarbons fraction into lower alkane and its corresponding alkene, where the corresponding alkene may be withdrawn from the distillation tower through a side outlet and the lower alkane may be withdrawn through a bottom outlet and directed back to the ODH reactor.

In an embodiment of this disclosure, the oxygen separation module is tubular and the oxygen transport membrane comprises an inner tube that is within an outer shell wherein a retentate side comprises the annular space between the inner tube and outer shell and a permeate side is the space within the inner tube.

In an embodiment of this disclosure, the chemical complex further comprises a fuel enhancement line upstream of the oxygen separation module for addition of supplemental combustible feedstock into the overhead stream feeding the oxygen separation module.

In an embodiment of this disclosure, the oxygen separation module further comprises means for heating said oxygen separation module to a temperature not less than 850° C.

In an embodiment of this disclosure, the chemical complex further comprises means for heating the overhead stream prior to entry into the oxygen separation module.

In an embodiment of this disclosure, the ODH reactor comprises more than one ODH reactor, each containing the same or different ODH catalyst, connected in series wherein the product stream from each reactor, except the last ODH reactor, is fed into a downstream ODH reactor.

The present disclosure also provides a process for ODH using the chemical complex described above.

In an embodiment of this disclosure, there is provided a process for the oxidative dehydrogenation of a lower alkane into a corresponding alkene using the chemical complex described previously, the process comprising:

i) contacting, in one or more oxidative dehydrogenation reactors and optionally in the presence of an inert diluent, an oxygen containing gas and a lower alkane containing gas with an oxidative dehydrogenation catalyst to produce a product stream comprising unreacted lower alkane and its corresponding alkene, inert diluent, unreacted oxygen, and possibly (optionally) one or more of:
  a. carbon oxides, including carbon dioxide and carbon monoxide;
  b. oxygenates, including but not limited to, one or more of acetic acid and maleic acid; and
  c. water;

ii) passing the product stream from i) through a quench tower to remove oxygenates and water from said product stream;

iii) passing the product stream from ii) through an amine wash to remove carbon dioxide from said product stream;

iv) passing the product stream from iii) through a drier to remove residual water;

v) passing the product stream from iv) through a distillation tower to separate an overhead stream comprising C1 hydrocarbons and inert diluent from C2/C2+ hydrocarbons;

vi) passing the overhead stream from v) and optionally a combustible fuel into one or both of the retentate side and the permeate side of an oxygen separation module; and vii) introducing air into said retentate side resulting in combustion of combustible C1 hydrocarbons and/or said combustible fuel generating heat to raise temperature of oxygen transport membrane to at least 850° C. permitting unreacted oxygen from said air to cross said oxygen transport membrane into permeate side producing oxygen enriched gas on permeate side and leaving oxygen depleted air on the retentate side;

viii) expelling said oxygen depleted air and combustion products through exhaust of said oxygen separation module; and ix) removing oxygen enriched gas and combustion products through the said outlet of said oxygen separation module; and x) directing said oxygen enriched gas back to i) as, or part of, the oxygen containing gas introduced into the one or more ODH reactors.

In an embodiment of this disclosure, the process further comprises that the oxygen enriched gas leaving the oxygen separation module comprises at least 50% oxygen.

In an embodiment of this disclosure, the process further comprises that the oxygen enriched gas leaving the oxygen separation module comprises less than 5% inert diluent.

In another embodiment of this disclosure, the process further comprises passing the product stream from i) through a heat exchanger before passing through the quench tower in ii).

In another embodiment of this disclosure, the process further comprises passing the product stream from iii) through a caustic wash before passing through the drier in iv).

In another embodiment of this disclosure, the process further comprises adding a low pH compound to the quench tower during removal of water and oxygenates from the product stream from i).

DETAILED DESCRIPTION OF THE PREFERRED EMBODIMENTS

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

The present disclosure relates to oxidative dehydrogenation (ODH) of lower alkanes into corresponding alkenes. In one aspect of this disclosure, there is a chemical complex useful for ODH, and, in another aspect, there is described a process for ODH that may be performed in the chemical complex outlined in the first aspect. Lower alkanes are intended to include saturated hydrocarbons with from 2 to 6 carbons, and the corresponding alkene includes hydrocarbons with the same number of carbons, but with a single double carbon to carbon bond. For ethane, ethylene is its corresponding alkene.

In the following description of the present disclosure, for reference to the figures, it should be noted that like parts are designated by like reference numbers.

Figure 1:
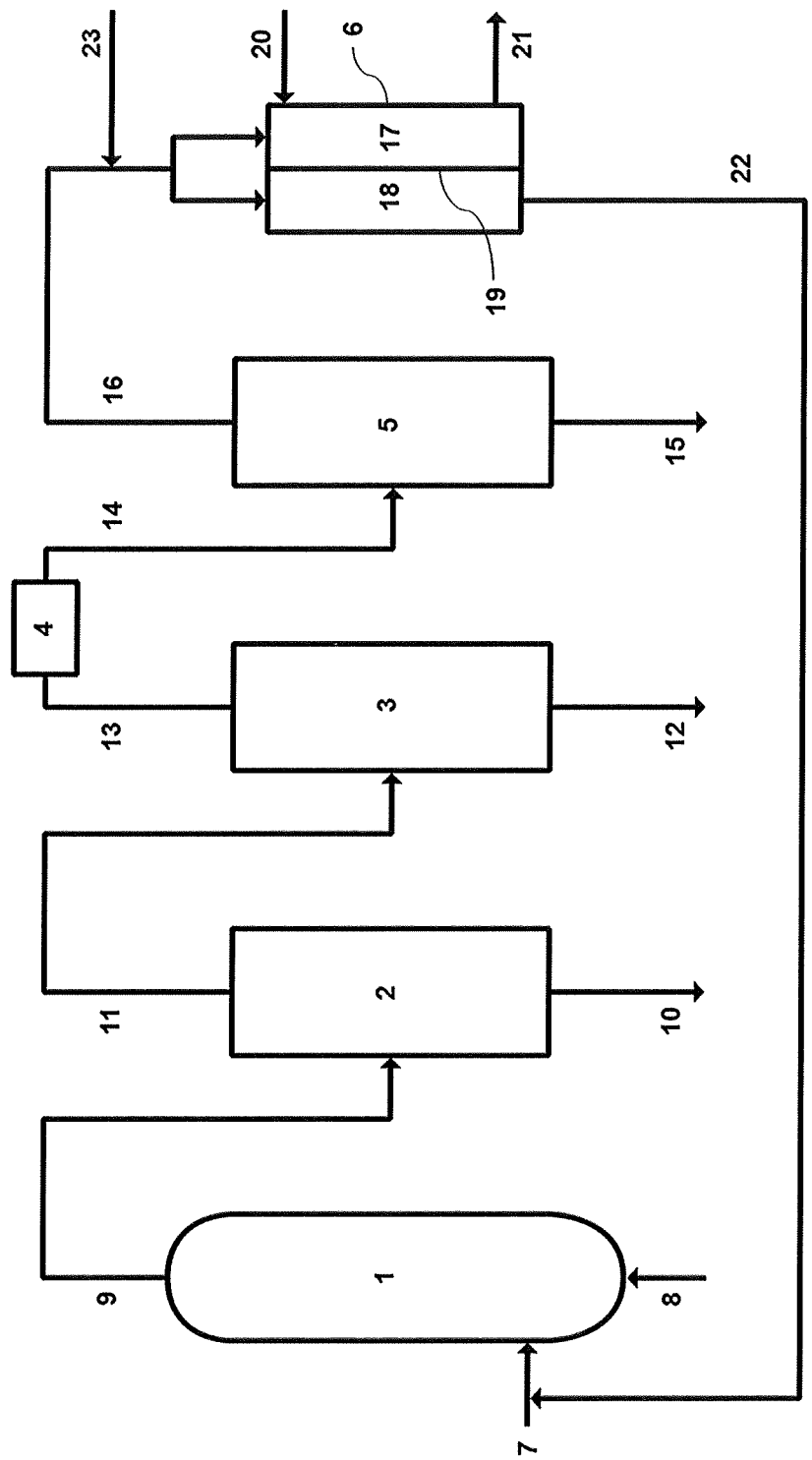
FIG. 1—Schematic of chemical complex of the present disclosure.

The chemical complex of the present disclosure, shown in one embodiment schematically in FIG. 1, comprises, in cooperative arrangement, an ODH reactor 1, a quench tower 2, an amine wash tower 3, a drier 4, a distillation tower 5, and an oxygen separation module 6. ODH reactor 1 comprises an ODH catalyst capable of catalyzing, in the presence of oxygen, which may be introduced via oxygen line 7, the oxidative dehydrogenation of lower alkane introduced via alkane line 8. The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 1 may also produce, depending on the catalyst and the prevailing conditions within ODH reactor 1, a variety of other products which may include carbon dioxide, carbon monoxide, oxygenates, and water. These products leave ODH reactor 1, along with unreacted alkane, corresponding alkene, residual oxygen, and inert diluent, if added, via ODH reactor product line 9.

ODH reactor product line 9 is directed to quench tower 2 which quenches the products from product line 9, and facilitates removal of oxygenates and water via quench tower bottom outlet 10. Unconverted lower alkane, corresponding alkene, unreacted oxygen, carbon dioxide, carbon monoxide, and inert diluent added to quench tower 2 exit through quench tower overhead line 11 and are directed into amine wash tower 3. Carbon dioxide present in quench tower overhead line 11 is isolated by amine wash tower 3, and captured via carbon dioxide bottom outlet 12 and may be sold, or, alternatively, may be recycled back to ODH reactor 1 as inert diluent (not shown). Products introduced into amine wash tower 3 via quench tower overhead line 11, other than carbon dioxide, leave amine wash tower 3 through amine wash tower overhead line 13 and are passed through a dryer 4 before being directed via stream 14 to distillation tower 5, where C2/C2+ hydrocarbons are isolated and removed via C2/C2+ hydrocarbons bottom outlet 15. The remainder comprises mainly C1 hydrocarbons, including remaining inert diluent and carbon monoxide, which leave distillation tower 5 via overhead stream 16 that is directed to oxygen separation module 6.

Oxygen separation module 6 comprises a sealed vessel having a retentate side 17 and a permeate side 18, separated by oxygen transport membrane 19. Overhead stream 16 may be directed into either of retentate side 17 or permeate side 18. Optionally, a flow controlling means 26 (FIG. 3D) may be included that allows for flow into both sides at varying levels. In that instance, an operator may choose what portion of the flow from overhead stream 16 enters retentate side 17 and what portion enters permeate side 18. Depending upon conditions, an operator may switch between the two sides, allow equivalent amounts to enter each side, or bias the amount directed to one of the two sides. Oxygen separation module 6 also comprises air input 20 for the introduction of atmospheric air, or other oxygen containing gas, into the retentate side 17. Combustion of products introduced into retentate side 17, due to the introduction of oxygen, may contribute to raising the temperature of oxygen transport membrane 19 to at least 850° C. so that oxygen can pass from retentate side 17 to permeate side 18. Components within the atmospheric air, or other oxygen containing gas, other than oxygen, cannot pass from retentate side 17 to permeate side 18 and can only leave oxygen separation module 6 via exhaust 21.

As a result of oxygen passing from retentate side 17 to permeate side 18, there is separation of oxygen from atmospheric air, or other oxygen containing gas, introduced into retentate side 17. The result is production of oxygen enriched gas on permeate side 18, which is then directed via oxygen enriched bottom line 22 to ODH reactor 1, either directly or in combination with oxygen line 7 (as shown in FIG. 1). When overhead stream 16 is directed into retentate side 17 the degree of purity of oxygen in oxygen enriched bottom line 22 can approach 99%. Conversely, when overhead stream 16 is directed into permeate side 18, the degree of purity of oxygen in oxygen enriched bottom line 22 is lower, with an upper limit ranging from 80 to 90% oxygen; the balance in the form of carbon dioxide, water, and remaining inert diluent, all of which do not affect the ODH reaction as contemplated by the present disclosure and can accompany the enriched oxygen into ODH reactor 1. Water and carbon dioxide are ultimately removed by quench tower 2 and amine wash tower 3, respectively. Indeed, one of the advantages of this disclosure is that carbon dioxide can be captured for sale as opposed to being flared where it contributes to greenhouse gas emissions. Alternatively, when carbon dioxide is used as the inert diluent, any carbon dioxide captured in the amine wash can be recycled back to ODH reactor 1 to perform its role as inert diluent.

Oxygen transport membrane 19 is temperature dependent, only allowing transport of oxygen when the temperature reaches at least 850° C. In some instances the components in overhead stream 16 by themselves are not capable, upon combustion in the presence of oxygen, to raise the temperature of oxygen transport membrane 19 to the required level. For this reason, the chemical complex described in this disclosure also comprises fuel enhancement line 23, upstream of oxygen separation module 6, where combustible fuel, for example methane, may be added to supplement the combustible products from overhead stream 16.

As previously noted, a concern for ODH is the mixing of a hydrocarbon with oxygen. Under certain conditions the mixture may be unstable and lead to an explosive event. U.S. Published Application No. 20180009662 titled "Inherently Safe Oxygen/Hydrocarbon Gas Mixer", inventor Vasily Simanzhenkov, assigned to Nova Chemicals Corporation, provides a means to mix a hydrocarbon containing gas with an oxygen containing gas in a flooded mixing vessel. By mixing in this way pockets of unstable compositions are surrounded by a non-flammable liquid so that even if an ignition event occurred it would be quenched immediately. Provided addition of the gases to the ODH reaction is controlled so that homogeneous mixtures fall outside of the flammability envelope, for the prescribed conditions with respect to temperature and pressure, the result is a safe homogeneous mixture of hydrocarbon and oxygen. Embodiments of this disclosure may be supplemented with a flooded gas mixer as described in the pending application.

Figure 2:
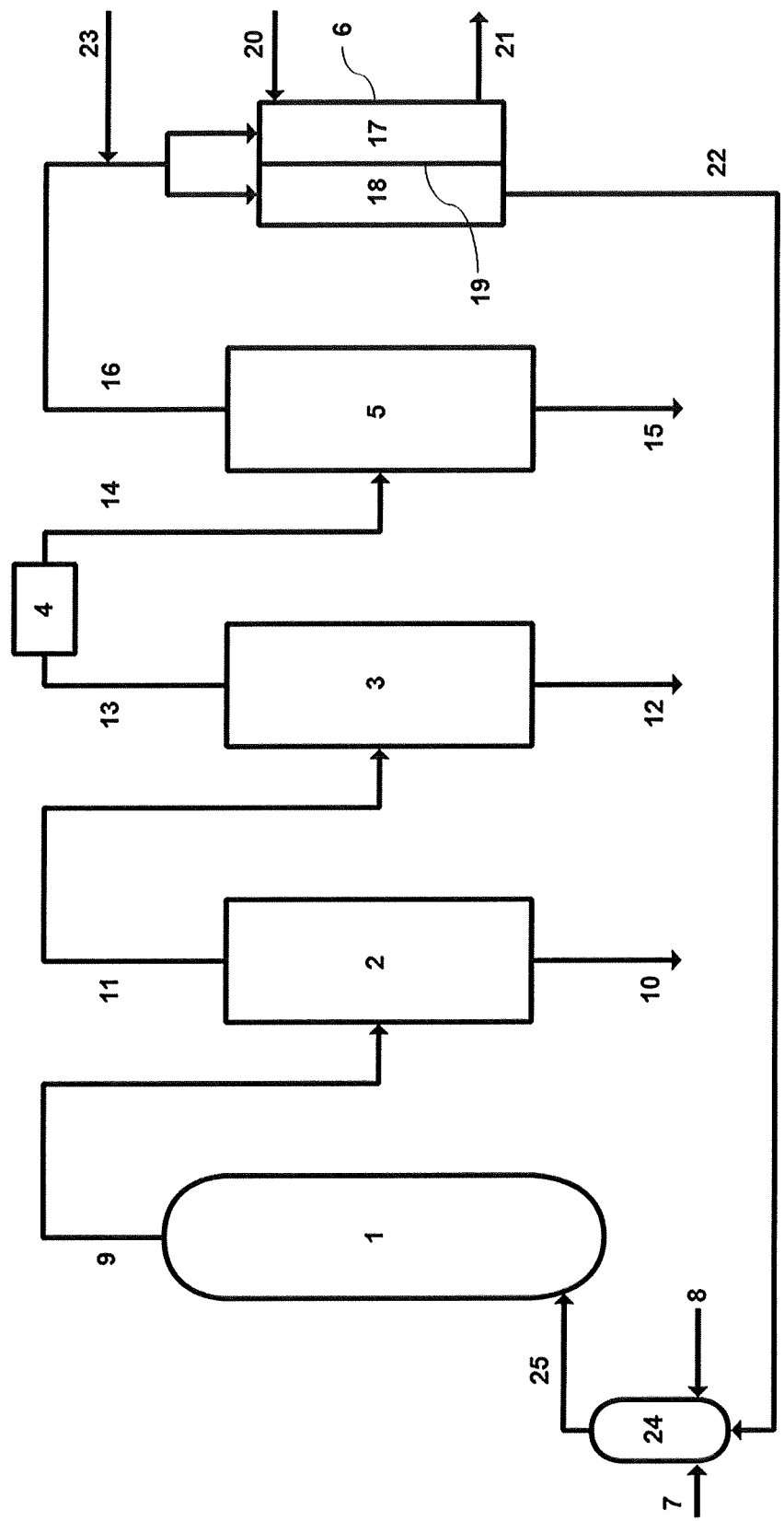
FIG. 2—Schematic of chemical complex of the present disclosure, showing alternative arrangement with presence of gas mixer.

In one embodiment of this disclosure, there is a flooded gas mixer 24 (FIG. 2) upstream of ODH reactor 1. In this instance, oxygen line 7 and alkane line 8 feed directly into flooded gas mixer 24. A homogeneous mixture comprising hydrocarbon and oxygen, and optionally an inert diluent, can be introduced into ODH reactor 1 from flooded gas mixer 24 via mixed line 25 (FIG. 2). Oxygen enriched bottom line 22 may feed directly into or in combination with oxygen line 7 into flooded gas mixer 24.

The temperature of the contents within product line 9, in a typical ODH process can reach 450° C. It may be desirable to lower the temperature of the stream before introduction into quench tower 2. In that instance, the present disclosure contemplates the use of a heat exchanger immediately downstream of each ODH reactor and immediately upstream of said quench tower 2. Use of a heat exchanger to lower temperatures in this fashion is well known in the art.

The present disclosure also contemplates use of various tools commonly used for chemical reactors, including flowmeters, compressors, valves, and sensors for measuring parameters such as temperature and pressure. It is expected that the person of ordinary skill in the art would include these components as deemed necessary for operation or for compliance with legal obligations related to safety regulations.

ODH Reactor

The present disclosure contemplates the use of any of the known reactor types applicable for the ODH of hydrocarbons. Particularly suited for use in this disclosure are conventional fixed bed reactors. In a typical fixed bed reactor, reactants are introduced into the reactor at one end, flow past an immobilized catalyst, products are formed and leave at the other end of the reactor. Designing a fixed bed reactor suitable for this disclosure may follow techniques known for reactors of this type. A person skilled in the art would know which features are required with respect to shape and dimensions, inputs for reactants, outputs for products, temperature and pressure control, and means for immobilizing the catalyst.

In one embodiment of this disclosure, the ODH reactor comprises a fixed bed reactor.

Also contemplated by the present disclosure is the use of a fluidized bed reactor. These types of reactors are also well known. Typically, the catalyst is supported by a porous structure, or distributor plate, located near a bottom end of the reactor, and reactants flow through at a velocity sufficient to fluidize the bed (e.g., the catalyst rises and begins to swirl around in a fluidized manner). The reactants are converted to products upon contact with the fluidized catalyst and subsequently removed from the upper end of the reactor. Design considerations include shape of the reactor and distributor plate, input and output, and temperature and pressure control, all of which would fall under knowledge of the person skilled in the art.

In another embodiment of this disclosure the ODH reactor comprises a fluidized bed reactor.

The present disclosure also contemplates multiple ODH reactors, either in series or in parallel. A swing bed type reactor is also envisioned in an embodiment. In this instance, parallel beds are alternatively exposed to a hydrocarbon feed comprising mainly hydrocarbons with optional residual oxygen, or an oxygen feed that is hydrocarbon free. The oxygen feed is directed to one reactor to re-oxidize a spent catalyst while simultaneously the hydrocarbon feed is passed through the other bed containing active oxidized catalyst, allowing ODH to occur. A valve configuration allows swinging the oxygen and hydrocarbon feeds between the two beds to regenerate the oxidized catalyst in one bed while ODH is occurring in the other bed. Use of multiple reactors, including ODH reactors, in either a parallel, series, or swing bed type arrangement is well known in the art.

In another embodiment of this disclosure the ODH reactor comprises multiple inlets for introduction of an oxygen containing gas. In this embodiment, oxygen addition is distributed in a staged manner throughout the reactor, limiting peak temperature increases by leveling oxygen concentration through the height or length of the reactor.

U.S. Pat. No. 9,545,610, entitled "Complex Comprising Oxidative Dehydrogenation Unit", inventor Simanzhenkov, assigned to Nova Chemicals (International) S.A. describes an ODH reactor where oxygen permeable ceramic tubes are placed inside of shell. In the description, this patent describes how ethane flows through the tube, while oxygen flows between the tubes and the outer shell. Oxygen can pass through the ceramic wall holding the catalyst, allowing conversion of ethane to ethylene at the interface between the ceramic wall and the interior of the tube. Ceramics are brittle by nature, and need to be reinforced or protected. This may be accomplished by incorporation of steel mesh on the interior and exterior surfaces of the ceramic tubes. This design provides the advantage that when a ceramic membrane loses integrity only excess oxygen enters that tube. Oxygen detectors located at the exit of each tube can detect the presence of excess oxygen, indicating the loss of integrity. The reactor can then be shut down safely and the damaged tube located and repaired. The present disclosure contemplates the use of this reactor design.

In an embodiment of this disclosure, the ODH reactor comprises an outer shell and one or more internal ceramic tubes defining a separate flow passage for ethane down the interior of said tubes and an annular passage between the external shell of the reactor and the ceramic tubes defining a flow path for an oxygen containing gas.

In another embodiment of this disclosure, the ceramic tubes further comprise an internal steel mesh and an external steel mesh.

ODH Catalyst

There are a number of catalysts which may be used in accordance with the present disclosure. The following catalyst systems may be used individually or in combination. One of ordinary skill in the art would understand that combinations should be tested at a laboratory scale to determine if there are any antagonistic effects when catalyst combinations are used.

The oxidative dehydrogenation catalyst of the present disclosure may be selected from the group consisting of:

i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1 (normalized), b=0.01 to 1.0, c=0.01 to 1.0, d=0.01 to 1.0, 0.00≤e≤0.10 and f is dependent on the oxidation state of the other elements, i.e. f is a number to satisfy the valence state of the catalyst;

ii) catalysts of the formula:

$$Ni_gA_hB_iD_jO_f$$

wherein: g is a number from 0.1 to 0.9, preferably from 0.3 to 0.9, more preferably from 0.5 to 0.85, most preferably 0.6 to 0.8; h is a number from 0.04 to 0.9; i is a number from 0 to 0.5; j is a number from 0 to 0.5; f is a number to satisfy the valence state of the catalyst; A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is selected from the group consisting of Ca, K, Mg, Li, Na, Sr, Ba, Cs, and Rb and mixtures thereof; and O is oxygen;

iii) catalysts of the formula:

$$Mo_aE_kG_lO_f$$

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg V, Ni, P, Pb, Sb, Si, Sn, Ti, U and mixtures thereof; and when a=1 (normalized); k is 0 to 2; l is 0 to 2, with the proviso that the total value of l for Co, Ni, Fe and mixtures thereof is less than 0.5; and f is a number to satisfy the valence state of the catalyst;

iv) catalysts of the formula:

$$V_mMo_nNb_oTe_pMe_qO_f$$

wherein: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

$$Mo_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; and when a=1.0 (normalized); r=0.05 to 1.0; s=0.001 to 1.0; t=0.001 to 1.0; u=0.001 to 0.5; and v=0.001 to 0.3; and f is a number to satisfy the valence state of the catalyst.

The above catalysts may be used individually or in combinations. One of ordinary skill in the art would be aware of the need to conduct routine tests to determine if there are antagonistic interactions between two or more catalyst which are being considered.

Methods of preparing the catalysts are known to those skilled in the art.

The present disclosure also contemplates that the ODH catalyst is supported. There are several ways that the ODH catalyst may be supported, all of which are well known in the art.

In one embodiment, the support may have a low surface area, preferably, less than 50 m²/g, more preferably, less than 20 m²/g. The support may be prepared by compression molding. At higher pressures, the interstices within the ceramic precursor being compressed collapse. Depending on the pressure exerted on the support precursor, the surface area of the support may be from about 20 to 5 m²/g, preferably, 18 to 10 m²/g.

There is a safety advantage to using low surface area supports in that there is a reduced probability that an interstitial space may be filled only with oxidant providing a source of ignition.

The low surface area support could be of any conventional shape, such as, spheres, rings, saddles, etc. These types of supports would be used in more conventional reactors where a mixed stream or sequential stream of gaseous reactants pass over the supported catalyst and the ethane is converted to ethylene. There are a number of other approaches in the prior art where, for example, a mixed bed of supported catalyst and a reversible metal oxide may be passed together through a reaction zone to release oxide to the reaction and then regenerate the oxide. In some embodiments, the reversible metal oxide may contact a screen or permeable membrane having the supported catalyst on the other side together with a stream of ethane to release oxygen to the reaction.

In an alternate embodiment described below, the catalyst may be supported on a surface of a permeable membrane defining at least part of the flow path for one reactant and the other reactant flows over the opposite surface of the ceramic to permit the oxidant and ethane to react on the ceramic surface.

It is important that the support be dried prior to use. Generally, the support may be heated at a temperature of at least 200° C. for up to 24 hours, typically, at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably, from 0.5 to 3 mmol/g of support.

The amount of the hydroxyl groups in silica may be determined according to the method disclosed by J. B. Peri and A. L. Hensley, Jr., in J. Phys. Chem., 72 (8), 2926, 1968, the entire contents of which are incorporated herein by reference.

The dried support may then be compressed into the required shape by compression molding. Depending on the particle size of the support, it may be combined with an inert binder to hold the shape of the compressed part.

The support for the catalyst may be a ceramic or ceramic precursor formed from oxides, dioxides, nitrides, carbides and phosphates selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof.

Preferred components for forming ceramic membranes include oxides of titanium, zirconium, aluminum, magnesium, silicon and mixtures thereof.

Typically, the catalyst loading on the support provides from 0.1 to 20 wt. % typically from 5 to 15 wt. %, preferably from 8 to 12 wt. % of said catalyst and from 99.9 to 80 wt. %, typically, from 85 to 95 wt. %, preferably from 88 to 92 wt. % of said support.

The catalyst may be added to the support in any number of ways. For example, the catalyst could be deposited from an aqueous slurry onto one of the surfaces of the low surface area support by impregnation, wash-coating, brushing or spraying. The catalyst could also be co-precipitated from a slurry with the ceramic precursor (e.g., alumina) to form the low surface area supported catalyst.

The support and catalyst may be combined and then comminuted to produce a fine particulate material having a particle size ranging from 1 to 100 micron. The comminution process may be any conventional process including ball and bead mills, both rotary stirred and vibratory, bar or tube mills, hammer mills, and grinding discs. A preferred method of comminution is a ball or bead mill.

The particulate catalyst may be used in an ODH reactor which may comprise single or multiple beds.

By-Product Removal

Oxidative dehydrogenation of alkanes inevitably produces not only corresponding alkenes, but other by-products as well. Depending on the conditions, including the catalyst type, the levels of by-products present downstream can range from minimal (less than 2%), to significant (greater than 2%). Even at minimal levels by-products are undesirable as they may interfere with downstream applications where the produced alkene is utilized. For ODH of lower alkanes, for example, ethane, the most common by-products include carbon oxides, including carbon monoxide and carbon dioxide, oxygenates, and water.

Typically, the separation of oxygenates and water from an ODH reactor product stream is achieved by using a quench tower. In the present disclosure, the term "oxygenates" refers to by-products of the oxidative dehydrogenation process that contain carbon, hydrogen, and oxygen, and include, but are not limited to, acetic acid, acrylic acid, and maleic acid. While the primary purpose of a quench tower is the cooling of a gaseous product stream, there is a secondary benefit for the purposes of the present disclosure. Cooling of the gaseous product line after leaving the reactor promotes condensation of water and oxygenates which can then be separated from the components that remain in the gaseous phase, namely the lower alkane, its corresponding alkene, and any carbon oxides. Some quench towers involve the spraying of water, or other liquid in which oxygenates are soluble, from the top of the tower onto the product stream entering from the bottom of the tower. Contact with water promotes cooling and ultimately condensation of the heavier components slated for removal.

In an embodiment of the present disclosure, a product stream containing unconverted alkane, corresponding alkene, residual oxygen and by-products are passed through a quench tower to remove water and oxygenates. The remainder is passed on for the next step of purification. Techniques of this nature have been thoroughly developed and are commonplace in the prior art. The person skilled in the art would understand how to integrate a quench tower into the chemical complex described in this disclosure.

The present disclosure also contemplates the use of multiple quench towers. Where multiple ODH reactors are employed it is preferred that each ODH reactor is followed by a quench tower, especially in instances where the reactors are in series. In this setting, oxygenates and water are removed before the remainder, optionally supplemented with additional oxygen, is passed on to the next ODH reactor in the series. In a parallel arrangement, the product streams from the parallel reactors may be combined before introduction into a quench tower.

Another common and well known separation method applicable for use with the present disclosure is the use of alkylamines, referred to herein as amines, in a scrubber to remove carbon dioxide from gaseous compositions. Carbon dioxide present in a gas is absorbed by aqueous amine solution which can then be separated from the remaining gaseous components. The amine is stripped of carbon dioxide by heating above 100° C. and recycled to continue the process, while water from the stripper vapor is condensed, leaving relatively pure carbon dioxide. The carbon dioxide, highly concentrated, can be captured and sold, or, alternatively it can be recycled back to act as an inert diluent for the lower alkane and oxygen containing gases when introduced into the ODH reactor. This is one advantage of the present disclosure. Carbon dioxide produced in the process can be captured instead of being flared where it contributes to greenhouse gas emissions. This becomes more relevant with the addition of the oxygen separator which also produces carbon dioxide.

Amine scrubbing has been used, especially in the petrochemical industry, for over sixty years. There is a plethora of prior art and common knowledge that is available to the person skilled in the art for design and operation of an amine scrubber (referred to as amine wash tower) for use with the present disclosure. Consideration of the type of amines used in the process requires special attention. Amines used vary in their ability to remove oxygen and in their tendency to promote the formation of degradation products. For example, monoethanolamine (MEA) is commonly used and is capable of removing a high percentage of carbon dioxide, even at low concentrations, but can also react with the carbon dioxide to form degradation products. This results in lower carbon dioxide capture and a reduction of available amines for subsequent absorption cycles.

The stream leaving the amine wash tower comprises unconverted lower alkane, corresponding alkene, and carbon monoxide, and possibly methane as a contaminant present in the original hydrocarbon feedstock. Inert diluent other than carbon dioxide, if used, may also be present in the stream leaving the amine wash tower. The stream leaving the amine wash tower will also likely contain water—carryover from the amine wash tower—that should be removed via a dryer prior to directing the stream to a distillation tower. This is essential when cryogenic distillation is employed as any water present in the stream may freeze in the distillation tower, causing problems related to plugging and fouling of the tower. Dehydration of gaseous compositions using a dryer is well known in the art. Methods include, but are not limited to, absorption using a sorbent such as triethyleneglycol (TEG), adsorption with at least two solid desiccant containing adsorption beds, and condensation. The product stream will preferably contain less than 50 ppm of water, more preferably less than 25 ppm of water, and most preferably less than 10 ppm of water, before being passed on to the next stage.

After removal of water, the present disclosure contemplates further separation of the product stream into an overhead stream and a C2/C2+ hydrocarbons stream using a distillation tower. The overhead steam comprises mainly C1 hydrocarbons (hydrocarbons with only one carbon), comprising mostly carbon monoxide but with the possibility of smaller amounts of methane, and inert diluent if used. The C2/C2+ hydrocarbons stream would comprise the unconverted lower alkane and its corresponding alkene, and any additional hydrocarbons (hydrocarbons containing 2 or more carbons), that were present as impurities in the original hydrocarbon feedstock added to the ODH reactor. Using a distillation tower for separation of C1 hydrocarbons and C2/C2+ hydrocarbons is well known in the art, and employs heating and cooling of gases in the presence of trays which capture condensed species. The spacing and number of trays dictate the degree of separation.

For the present disclosure the distillation tower comprises an upper outlet for removal of the overhead stream, and a lower outlet for removal of the remainder, including the higher weight C2/C2+ hydrocarbons. The overhead stream is directed toward the next step in the disclosed chemical complex, i.e. the oxygen separation module. The C2/C2+ hydrocarbons can then be directed to a C2+ splitter to separate the lower alkane from its corresponding alkene. The lower alkane can be fed back to the ODH reactor, and the corresponding alkene, the target product, can be captured and employed for use in a variety of applications that depend on the nature of the alkene. For example, if the desired product is ethylene then use in synthesis of polyethylene would be appropriate.

As mentioned, the degree of separation capable within a distillation tower is dependent upon the number of trays within the unit. The most common method involves cryogenic distillation so the nature of the species targeted for separation and their relative volatilities plays a role. For example, the relative volatility of ethylene to ethane is quite small. As a result, a tower designed to separate the two species would need to be tall and include a large number of trays. The difference in relative volatilities between C2/C2+ hydrocarbons and C1 hydrocarbons is significant enough that a smaller tower with fewer trays would suffice. In the present disclosure, a person skilled in the art would understand from this relationship that a smaller tower would be sufficient to separate out carbon monoxide and methane (C1 hydrocarbons), from the unconverted lower alkane and its corresponding alkene. However, if separation of the lower alkane with the corresponding alkene is also desired then a much larger tower would be needed. In that case, the tower would include another outlet, or side out where the corresponding alkene may be withdrawn from the distillation tower. Also contemplated is the separation of the lower alkane and corresponding alkene in a separate unit, after removal of the lower alkane and corresponding alkene from the distillation tower. Specifically, a splitter, which is well known in the art, may be used. In an embodiment of this disclosure, the stream of C2/C2+ hydrocarbons leaving the distillation tower is directed into a splitter.

In an embodiment of this disclosure the distillation tower comprises an outlet for removal of the overhead stream and an outlet for removal of the C2/C2+ hydrocarbons stream. In another embodiment of this disclosure the distillation tower comprises a side outlet for removal of alkenes.

Oxygen Separation Module

An embodiment of the oxygen separation module of this disclosure comprises a sealed vessel with two compartments, separated by a temperature dependent oxygen transport membrane, as shown in FIG. 1. The two compartments are the retentate side 17 and the permeate side 18. That the membrane is temperature dependent means that at a critical temperature the membrane will selectively allow oxygen to pass through from one side to the other. The oxygen separation module also comprises at least two inlets, air input 20 for introducing atmospheric air into the retentate side 17 and the other for introducing overhead stream 16 into either of the retentate side 17 or the permeate side 18, or both retentate side 17 and permeate side 18. Finally, there are two outputs from the oxygen separation module. There is exhaust 21 for removal of oxygen depleted air and combustion products from the retentate side, and an outlet for removal of oxygen enriched gas and possibly combustion products from the permeate side into oxygen enriched bottom line 22. The oxygen enriched gas, and possibly combustion products, may be recycled back as or part of the oxygen containing gas introduced into the ODH reactor.

In an embodiment of this disclosure the oxygen separation module 6 is depicted schematically in FIGS. 3A, 3B, 3C and 3D. The oxygen transport membrane 19 is a tube and fits inside a larger tube 27 which forms the outer wall of oxygen separation module 6. The annular space between the larger tube 27 and oxygen transport membrane 19 corresponds to the retentate side, while the space within oxygen transport membrane 19 corresponds to the permeate side. Material suitable for construction of the outer wall 27 include those resistant to temperatures that exceed 850° C. and approach 1000° C., selection of which falls within the knowledge of the skilled worker.

Figure 3A:
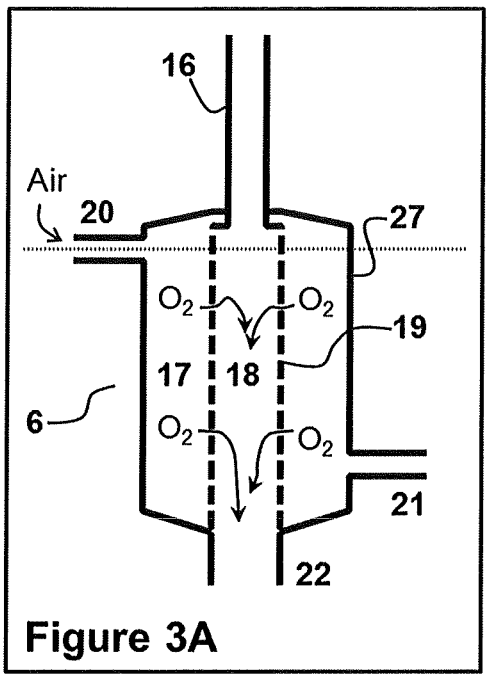
FIG. 3A—Schematic of embodiment of oxygen separation module where C1 hydrocarbon containing line 16 is directed to permeate side.
Figure 3B:
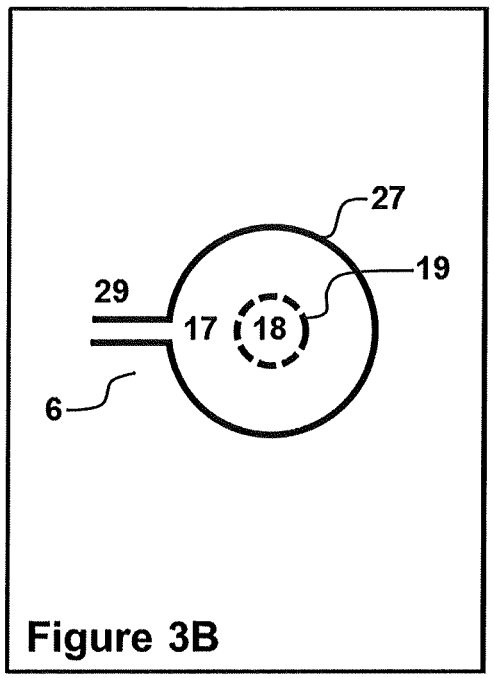
FIG. 3B—Cross section of oxygen separation module through dotted line present in FIGS. 3A, C, and D.
Figure 3C:
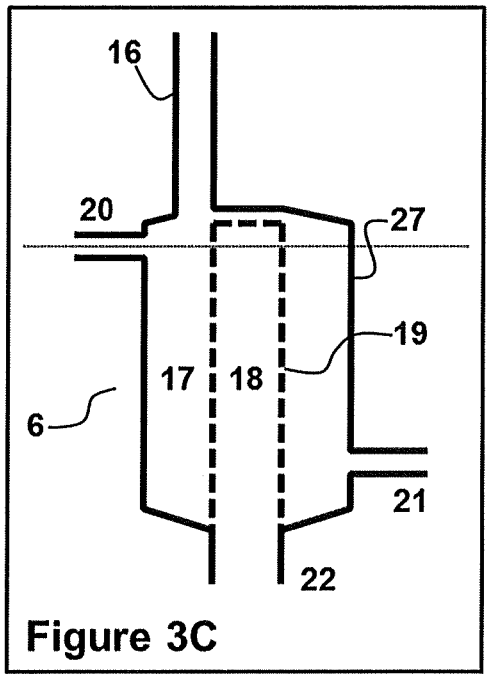
FIG. 3C—Schematic of embodiment of oxygen separation module where C1 hydrocarbon containing line 16 is directed to the retentate side.
Figure 3D:
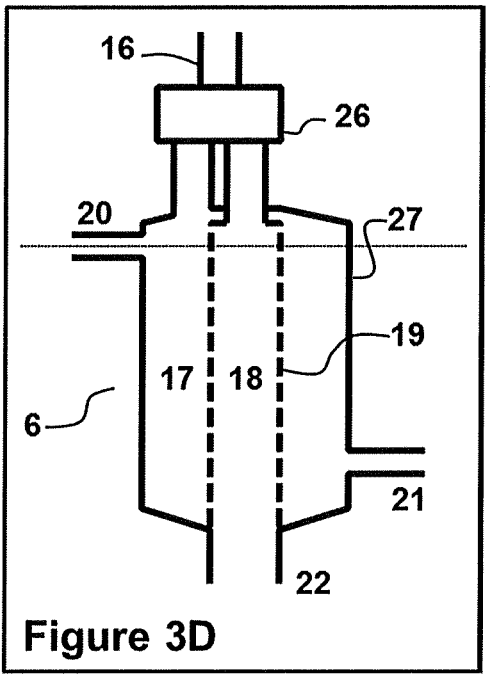
FIG. 3D—Schematic of embodiment of oxygen separation module where C1 hydrocarbon containing line 16 can be directed to either of or both the permeate side and the retentate side.

The present disclosure contemplates the inlet for the overhead stream entering the oxygen separation module 6 into either of the permeate side (FIG. 3A) or the retentate side (FIG. 3C). This disclosure also contemplates the use of a valve for switching between directing the overhead stream to the retentate side or the permeate side. This would allow an operator to choose which of the sides, permeate or retentate, that the overhead stream is directed to.

Finally, the present disclosure also contemplates introducing the overhead stream into both the retentate side and permeate side simultaneously. This includes the ability to alter the relative amount of overhead stream which is entered into each side. For example, an operator may choose to permit 80% of the overhead stream to enter into the retentate side and only 20% to the permeate side, or vice versa. To be clear, the amount of the overhead stream that enters either side, permeate or retentate, can range from 0 to 100%, with the fraction for each side totaling 100%. Precision valves that can control the flow sent to either side are well known in the art, and include, without limitation, solenoid valves, ball valves, or a combination of a back-pressure needle valve and solenoid valve.

The oxygen transport membrane component of the oxygen separation module selectively allows passage of oxygen when the membrane reaches a critical temperature. Membranes of this nature are known. Specifically, a Mixed Ionic-Electronic Conducting (MIEC) membrane is contemplated for use in this disclosure. Movement of oxygen across the membrane is driven by an oxygen partial pressure gradient, moving from the high oxygen partial pressure side to the low oxygen partial pressure side. To get the oxygen to move to the permeate side, a skilled operator would understand that the partial pressure of oxygen on the retentate side would need to be increased to the point where it equals or exceeds the partial pressure of oxygen on the permeate side. For example, if oxygen on the permeate side is close to 100% of the volume at a pressure of the 1 atm, then the pressure on the retentate side would need to be increased to at least 5 atm when atmospheric air is added and contains approximately 21% oxygen by volume. Alternatively, the pressure on the permeate side could be reduced to levels at or below 0.2 atm using a vacuum driven process.

Also contemplated in the design of the oxygen separation module is the ability to add a sweep gas, such as, steam or carbon dioxide, to the permeate side to dilute oxygen that crosses over from the retentate side. The effect of the sweep gas is the lowering of the oxygen partial pressure on the permeate side to drive diffusion of oxygen from the retentate side. A result of this configuration is a much lower percentage of oxygen within the oxygen enriched bottom line 22, as it is diluted by the sweep gas. Theoretically, the oxygen percentage could drop well below 10%. However, if water is the sweep gas, then a heat exchanger downstream of oxygen separation module 6 can be used to remove the water following condensation, increasing the relative amount of oxygen in the line. If carbon dioxide is used then an operator can determine the amount required to produce the desired oxygen level in the oxygen enriched bottom line 22. By altering the amount of sweep gas an operator can control how much oxygen is present in the line as it leaves the oxygen separation module. A person skilled person in the art would understand this relationship and would be familiar with using a sweep gas and with using means for controlling the pressure in a sealed vessel, such as, the type contemplated for the oxygen separation module described in this disclosure.

It is well known that oxygen flux across the membrane is dependent upon the thickness of the membrane. A thin membrane allows oxygen to cross more quickly than a thick membrane. A membrane comprised of a single layer, or monolithic type membrane, may be reduced in thicknesses in the range of 0.1 to 0.2 µM to allow greater oxygen flux. However, these thicknesses are not practical due to susceptibility to mechanical instability. If a monolithic membrane is to be used, thicknesses below 0.2 mm are not recommended. Other known membrane configurations include asymmetric membranes where a very thin conducting layer is supported on both sides by a porous structure. This allows a user to employ very thin membranes that allow higher oxygen flux without sacrificing stability. It is not essential to use any particular membrane structure provided the oxygen flux across the membrane is sufficient. In the present disclosure the oxygen transport membrane has an oxygen flux within the range of 300 to 1500 $l/hr*m^2$, more preferably from 500 to 1300 $l/hr*m^2$, and most preferably from 700 to 1000 $l/hr*m^2$.

Theoretically, the oxygen transport membrane can reach 850° C. due to the exothermic nature of combustion of the C1 hydrocarbons present in the overhead stream. However, in instances where the C1 hydrocarbons (as the sole source of feedstock for combustion) are insufficient to reach the required temperature, the present disclosure contemplates the addition of combustible fuel to the oxygen separation module to include an independent means for heating the oxygen separation module, including the oxygen transport membrane. For instance a separate line may add a combustible fuel, for example, methane, either into the overhead stream before entering the oxygen separation module (e.g., line 23 in FIG. 1), or directly into the oxygen separation module. Alternatively a heat exchanger or other means may be employed to heat the module to the required temperature. It is preferred that when using a heat exchanger or other means for heating that heat is distributed evenly throughout the module. The present disclosure also contemplates heating the overhead stream just upstream of the oxygen separation module.

During start-up of the chemical complex, the oxygen transport membrane may not be at the required temperature. As a result, oxygen from the injected air cannot pass into the permeate side. In this instance, it would be preferable to direct the overhead stream solely into the retentate side so that combustion on that side can contribute to increasing the temperature of the oxygen transport membrane to the point where oxygen can cross. When at steady state and the temperature of the oxygen transport membrane exceeds 850° C., the overhead stream may be directed to either side because oxygen can freely pass and permit combustion such that heat is continuously generated. Alternatively, during startup, other means, such as a heat exchanger, may be used to heat the membrane.

ODH Process

Use of the ODH reactor as described in the chemical complex of the present disclosure falls within the knowledge of the person skilled in the art. For best results, the oxidative dehydrogenation of a lower alkane may be conducted at temperatures from 300° C. to 550° C., typically, from 300° C. to 500° C., preferably, from 350° C. to 450° C., at pressures from 0.5 to 100 psi (3.447 to 689.47 kPa), preferably, from 15 to 50 psi (103.4 to 344.73 kPa), and the residence time of the lower alkane in the reactor is typically from 0.002 to 30 seconds, preferably, from 1 to 10 seconds.

The lower alkane containing gas is ideally of a purity greater than 95%, most preferably, 98%. In an embodiment of this disclosure, the process includes the addition of an ethane containing gas of purity of preferably, 95%, most preferably, 98%.

Preferably, the process has a selectivity for the corresponding alkene (ethylene in the case of ethane ODH) of greater than 95%, preferably, greater than 98%. The gas hourly space velocity (GHSV) will be from 500 to 30000 $h^{-1}$, preferably greater than 1000 $h^{-1}$. The space-time yield of corresponding alkene (productivity) in g/hour per kg of the catalyst should be not less than 900, preferably, greater than 1500, most preferably, greater than 3000, most desirably, greater than 3500 at 350 to 400° C. It should be noted that the productivity of the catalyst will increase with increasing temperature until the selectivity is sacrificed.

When the lower alkane is ethane, the specificity of conversion to ethylene should be not less than 80%, preferably, greater than 90%, most preferably, 95% or greater.

Safety of the process is a primary concern. For that reason, mixtures of a lower alkane with oxygen should comprise ratios that fall outside of the flammability envelope. The present disclosure contemplates that a ratio of alkane to oxygen may fall outside the upper flammability envelope. In this instance the percentage of oxygen in the mixture is not greater than 30%, preferably not greater than 25%, most preferably not greater than 20%.

With higher oxygen percentages, it is imperative to choose alkane percentages that keep the mixture outside of the flammability envelope. While a person skilled in the art would be able to determine an appropriate level it is recommended that the percentage of alkane not exceed 40%. For instances where the mixture of gases prior to ODH comprises 20% oxygen and 40% alkane, the balance must be made up with an inert diluent, such as nitrogen, carbon dioxide, or steam. The inert diluent should exist in the gaseous state in the conditions within the reactor and should not increase the flammability of the hydrocarbon added to the reactor, characteristics that a skilled worker would understand when deciding on which inert diluent to employ. Inert diluent can be added to either of the lower alkane containing gas or the oxygen containing gas prior to entering the ODH reactor or may be added directly into the ODH reactor.

While the present disclosure contemplates use of ratios of lower alkane to oxygen that do not equal or approximate 1:1, it is preferable that the addition of each is close to 1:1. The reason for this is that the goal is for 100% conversion, with minimal unreacted alkane and oxygen leaving the ODH reactor. When the components are added in an unbalanced ratio the presence of oxygen or unreacted alkane in the product stream is inevitable. In one embodiment, the product stream leaving the ODH reactor contains less than 5% unreacted lower alkane, preferably less than 2.5%, most preferably less than 1%. In another embodiment, the product stream leaving the ODH reactor contains less than 2% oxygen, preferably less than 1.5% oxygen, most preferably less than 1% oxygen.

The ratio of oxygen to lower alkane added to the ODH reactor may also effect the composition and contribution of by-products to the product stream leaving the ODH reactor. Excess oxygen may oxidize the corresponding alkene to a carboxylic acid. For example, ethylene produced in the ODH reactor may be further oxidized to acetic acid. Depending upon the desired product this may be desirable. A skilled operator would understand how changing the ratio of added gases, in combination with ODH catalyst selection, alters the products present in the stream leaving the ODH reactor.

Removal of by-products such as oxygenates, for example acetic acid, is routine for operators skilled in these types of processes. The quench tower, which is primarily used to reduce the temperature of the product stream, may be used to isolate oxygenates and water produced in the ODH reactor. The cooling of the product stream results in condensation of oxygenates at a much higher temperature than the dew point of the alkanes or the corresponding alkene gases. By taking advantage of this difference operators may capture the condensed products and allow the gaseous remains to move on to the next step in the separation of by-products from the product stream. Captured oxygenates may be used in other well-known downstream processes. For example, in ODH of ethane to ethylene, the ethylene may be further oxidized to acetic acid, which may be reacted with ethylene to produce vinyl acetate or other oxygenates.

The present disclosure also contemplates the addition of low pH compounds to the quench tower which has the effect of improving removal of oxygenates. In the absence of addition of low pH compounds it is possible that not all oxygenates will undergo condensation within the quench tower. In this case, any gaseous residual oxygenates may be passed on to the next stage. Addition of a low pH compound, such as sodium bicarbonate, may promote conversion of oxygenates into compounds with a higher dew point, increasing the likelihood of condensation.

Removal of carbon dioxide from the product stream, in combination with the oxygen separation module, is one of the advantages of the present disclosure. Carbon dioxide produced in the oxygen separation module, due to combustion on the permeate side of the oxygen transport membrane, can be captured, instead of being released to the atmosphere. The oxygen enriched gas and associated combustion products that are recycled back re-enter the chemical complex so that any carbon dioxide present can be isolated in the amine wash. Furthermore, the present disclosure also contemplates recycling the carbon dioxide isolated by the amine wash back to the ODH reactor, where it can be used as the inert diluent.

While ODH does not produce significant amounts of carbon dioxide, it does produce carbon monoxide, which ordinarily would be flared into the atmosphere when the opportunity to convert the carbon monoxide to value added chemicals is not feasible at the manufacturing site. The present disclosure allows the combustion of the carbon monoxide in a system that captures the resulting carbon dioxide and shuttles it back through the ODH chemical complex where it can be captured.

It should be noted that, theoretically, removal of oxygenates and carbon dioxide prior to oxygen separation is not absolutely essential. It is conceivable to pass the product stream from the ODH reactor directly to an oxygen separation module. However, in this instance the target alkene would be subjected to combustion and lost, defeating the purpose of the ODH reaction. It is necessary to separate the target alkene prior to oxygen separation. The present disclosure includes separation of unconverted alkane and corresponding alkene from the lighter C1 hydrocarbons using a cryogenic distillation process. The presence of oxygenates, such as acetic acid, and carbon dioxide would severely impact the function of a cryogenic distillation process. For this reason the present disclosure considers the removal of oxygenates and carbon dioxide as essential for success when using a process described herein.

The amine wash results in addition of water into the product stream, which must be removed prior to distillation.

As previously discussed dehydration of gaseous compositions falls within the common general knowledge of those skilled in the art.

Distillation of gaseous products and separation of components is also well known in the art. The skilled worker would know how to use a distillation tower to separate C1 hydrocarbons from C2/C2+ hydrocarbons.

The process of ODH as it relates to oxygen separation may vary, mostly dependent upon the temperature of the oxygen transport membrane. When the oxygen transport membrane is below the temperature at which oxygen can selectively pass through, the preferred embodiment is to direct the overhead stream into the retentate side, where atmospheric air is introduced. In this situation the oxygen within the air is present for the combustion of the C1 hydrocarbons present in the overhead stream. An operator must judge on whether the degree to which this combustion raises the temperature of the oxygen transport membrane is significant enough for selective oxygen transport to occur. If it is insufficient, meaning the temperature does not surpass 850° C., regardless of the amount of C1 hydrocarbon gas flowing into the module, then additional combustible fuel may be added. For example, adding methane to the overhead stream may be sufficient to reach the required temperature.

Provided enough combustion is occurring with addition of combustible fuel and the temperature of the membrane is above 850° C. then the combustible fuel or the overhead stream may be directed into the permeate side. The reason this is possible is that since the membrane is hot enough, oxygen can pass through and act on the C1 hydrocarbons present in the overhead stream and added to the permeate side, releasing heat so as to maintain the membrane in an oxygen transport able mode. Where the overhead stream is directed to depends on the desired degree of oxygen separation. When directed to the retentate side, combustion results in production of water and carbon dioxide, which cannot pass through and are therefore ejected through the exhaust. In this mode, it is not possible to capture the carbon dioxide produced in the chemical complex described. There are other modes for capture that may be involved, but are not integrated into the ODH chemical complex. The oxygen that passes in this configuration is unaccompanied by the combustion products and therefore is of very high purity. In an embodiment of this disclosure the overhead stream is directed to the retentate side and the oxygen enriched stream comprises at least 95% oxygen, preferably 98% oxygen, most preferably 99% oxygen.

In the alternative, the overhead stream may be directed into the permeate side. In this setting the oxygen transport membrane must be at the required temperature. In this case the C1 hydrocarbons within the overhead stream and added to the permeate side are subjected to combustion with the oxygen crossing the membrane. Any unreacted oxygen and the combustion products are mixed before leaving. As a result the oxygen is diluted and the oxygen enriched stream contains a lower degree of oxygen. The degree of oxygen dilution may also be significantly increased when a sweep gas is employed, even approaching levels below 10%. In an embodiment of this disclosure the overhead stream is directed to the permeate side and the oxygen enriched stream comprises at least 20% oxygen, preferably 55% oxygen, most preferably 90% oxygen, with the balance comprising carbon dioxide and water, and possibly inert diluent.

Optimization of the process requires an operator to understand that the side to which the overhead stream is directed will impact on the fate of carbon dioxide produced and the degree to which carbon dioxide contributes to the oxygen enriched gas directed back. Since carbon dioxide is a suitable inert diluent for dilution of the lower alkane and oxygen containing gases it is expected that an operator may adjust the ratio of the overhead stream entering into the retentate side relative to the permeate side so as to produce an oxygen enriched gas with a desired level of carbon dioxide. Ideally, the level will be adjusted so that when combined with carbon dioxide isolated by the amine wash the total amount will equal the amount required for dilution of the lower alkane and oxygen containing gases while at the same time minimizing the amount of carbon dioxide released into the atmosphere after ejection from the oxygen separation module exhaust.

In an embodiment of this disclosure the entirety of the carbon dioxide isolated in the amine wash is recycled back as inert diluent and the ratio of the overhead stream entering the retentate side relative to the permeate side is altered to allow for production of oxygen enriched gas with a degree of carbon dioxide that when mixed with carbon dioxide from the amine wash falls within the levels required for a safe mixture with the lower alkane containing gas.

This disclosure will further be described by reference to the following examples. The following examples are merely illustrative of this disclosure and are not intended to be limiting. Unless otherwise indicated, all percentages are by weight.

EXAMPLES

A kinetic model was developed using Aspen Plus V8.6 software and used in simulations to predict production rates of various species following oxidative hydrogenation of ethane using a fixed bed reactor. The simulation data for various feed compositions and temperature/pressure conditions was compared to experimental data collected from ODH of ethane using a fixed bed reactor under the conditions described below.

ODH Reaction Conditions

ODH of ethane was performed using two bench scale fixed bed tubular reactors, in series, constructed with SS316L stainless steel tubes having an optical diameter of 1.0" and a length of 34". Each reactor was wrapped in an electrical heating jacket and sealed with ceramic insulating material. Temperature within the reactors was monitored using a 7 point thermocouple. The catalyst bed in each reactor comprised 150 g in total weight of catalyst having the formula $MoV_{0.40}Nb_{0.16}Te_{0.14}O$, with relative atomic amounts of each component, relative to a relative amount of Mo of 1, shown in subscript. The catalyst bed was secured in place by packing quartz powder above and below the bed, with glass wool on the top and bottom of the reactor tube to prevent bed movement during experimental runs.

For experimental runs the reaction pressure was ~1 bar with flow through the reactor having a weight hourly space velocity (WHSV) of 0.68 $h^{-1}$. Three separate runs were completed with temperatures of 316° C. (Run 1), 332° C. (Run 2), and 336° C. (Run 3). A feed composition of ethane, ethylene, oxygen, and carbon dioxide in weight percent (wt %) of 43/0/22/35, premixed, was introduced into reactor 1. The mole fraction of each component produced in the reactors was measured downstream of reactor 2. The results for each experimental run were compared to results obtained with the same conditions using the kinetic model (see Table 1). There is excellent agreement between the experimental runs and the simulation, as seen by the R squared values which range from 0.9933 to 0.9961.

TABLE 1

Comparison of experimental data (EXP) on fixed bed reactor unit with kinetic model simulation data (SIM)

|  | Run 1 | | Run 2 | | Run 3 | |
| --- | --- | --- | --- | --- | --- | --- |
| Temperature (° C.) | 316 | | 332 | | 336 | |
| Pressure (bar) | 0.94 | | 0.98 | | 0.99 | |
| Mole fraction | EXP | SIM | EXP | SIM | EXP | SIM |
| Ethane ($C_2H_6$) | 0.376 | 0.380 | 0.303 | 0.312 | 0.294 | 0.297 |
| Ethylene ($C_2H_4$) | 0.080 | 0.078 | 0.113 | 0.120 | 0.122 | 0.129 |
| Oxygen ($O_2$) | 0.158 | 0.156 | 0.097 | 0.097 | 0.085 | 0.082 |
| Steam ($H_2O$) | 0.090 | 0.107 | 0.181 | 0.179 | 0.181 | 0.196 |
| Carbon dioxide ($CO_2$) | 0.278 | 0.267 | 0.269 | 0.268 | 0.276 | 0.269 |
| Carbon monoxide (CO) | 0.014 | 0.009 | 0.030 | 0.018 | 0.035 | 0.020 |
| Acetic acid ($CH_3COOH$) | 0.004 | 0.003 | 0.007 | 0.005 | 0.007 | 0.006 |
| R squared ($R^2$) | 0.9961 | | 0.9975 | | 0.9933 | |

Chemical Complex Simulation

Following confirmation that the kinetic model provides reasonable estimates for the values of products produced in the ODH reactor, further simulations were conducted on a speculative chemical complex comparable to the present disclosure but without the final oxygen separation module. An ethane ODH simulation was performed with a target ethylene production rate of 20 kg/hr, using of a flow rate, in kg/hr, of ethane entering the ODH reactor 1 of approximately 23.38 kg/hr, (stream 8) and of oxygen (stream 7) of approximately 16.72 kg/hr, diluted in a stream of carbon dioxide flowing at a rate of 28.61 kg/hr (also stream 7). The simulation took into account that ethane feedstock is frequently contaminated with trace amounts of propane and methane. Simulated results of the composition for various components within each stream are shown in Table 2, along with the temperature and pressure at the points where measurements were taken. For the purposes of clarity, trace elements were not included (e.g., hydroxide radicals). The results fall within the ranges expected under the simulated ODH conditions. The flow rate of carbon dioxide coming out of the amine wash tower 3 in carbon dioxide bottom outlet 12 of 29.61 kg/hr would be sufficient to provide enough inert diluent flowing into the ODH reactor 1.

Oxygen Separation Module Simulation

To ascertain whether the combustible C1 hydrocarbons present in overhead stream 16 coming off of the distillation tower 5 would be sufficient feedstock to raise the temperature of the oxygen transport membrane to the required temperature, an additional model was created using Aspen Plus V8.6. The Rstoic block in Aspen was used to simulate the adiabatic combustion process. Development of the model assumed that the oxygen transport membrane can permeate $O_2$ from the retentate side to the permeate side with 100% selectivity only when the membrane module operating temperature is ≥850° C. The values of the various components present in overhead stream 16 from the previous simulation were used in the model (e.g., 0.20 kg/hr carbon monoxide and 0.35 kg/hr methane). Four scenarios were modeled, differing in whether additional combustible fuel was added via line 23 (FIGS. 1 and 2) and to which side of the membrane the overhead stream was directed. In Case 0, no additional combustible fuel was added to overhead stream 16, 100% of which was added to the retentate side. Case 1—a flow rate of 2.1 kg/hr of methane was added via line 23 to the overhead stream 16, which was directed to the retentate side. Case 2—a flow of rate of 2.1 kg/hr of methane was added via line 23 to the overhead stream 16, which was directed to the permeate side. Case 3—a flow rate of 2.1 kg/hr of methane was added via line 23 to the overhead stream 16, 50% of which was directed to the retentate side and 50% was directed to the permeate side. The simulation using these conditions was used to estimate the temperature within the oxygen separation module and the rates of flow for the various components coming out of the oxygen separation module via oxygen enriched bottom line 22, shown in Table 3.

TABLE 3

Simulation results for oxygen separation module

|  | Case 0 | Case 1 | Case 2 | Case 3 |
| --- | --- | --- | --- | --- |
| Methane added via line 23 (kg/hr) | 0 | 2.1 | 2.1 | 2.1 |
| Fraction of overhead stream 16 into retentate side | 100% | 100% | 0% | 50% |
| Fraction of overhead stream 16 into permeate side | 0% | 0% | 100% | 50% |
| Temperature (° C.) | 568 | 850 | 850 | 850 |
| Pressure (kPa(g)) | 101 | 101 | 101 | 101 |
| Flow rates (kg/hr) of components leaving the oxygen separation module via oxygen enriched bottom line 22. | | | | |
| Carbon monoxide (CO) | 0 | 0 | 0 | 0 |
| Carbon dioxide ($CO_2$) | 0 | 0 | 3.00 | 1.60 |

TABLE 2

Stream properties at locations within the chemical complex

| Stream | 7 | 8 | 9 | 10 | 11 | 12 | 13 | 15 | 16 |
| --- | --- | --- | --- | --- | --- | --- | --- | --- | --- |
| Temperature (° C.) | 299.1 | 299.1 | 104.1 | 103.7 | 56.4 | 48.9 | 29.5 | −38.8 | −126.3 |
| Pressure (kPag) | 285.0 | 285.0 | 208.4 | 207.7 | 557.9 | 14.1 | 413.6 | 1425.0 | 1400.0 |
| Mass Flow (kg/hr) | | | | | | | | | |
| Ethane ($C_2H_6$) | 0.00 | 23.38 | 0.00 | 0.00 | 0.00 | 0.00 | 0.00 | 0.00 | 0.00 |
| Ethylene ($C_2H_4$) | 0.16 | 0.00 | 20.16 | 0.00 | 20.15 | 0.17 | 19.99 | 19.98 | 0.01 |
| Methane ($CH_4$) | 0.00 | 0.36 | 0.36 | 0.00 | 0.36 | 0.00 | 0.36 | 0.01 | 0.35 |
| Propane ($C_3H_8$) | 0.00 | 0.39 | 0.00 | 0.00 | 0.00 | 0.00 | 0.00 | 0.00 | 0.00 |
| Carbon dioxide ($CO_2$) | 28.61 | 0.00 | 30.56 | 0.01 | 30.54 | 29.61 | 0.00 | 0.00 | 0.00 |
| Carbon monoxide (CO) | 0.00 | 0.00 | 0.27 | 0.00 | 0.27 | 0.00 | 0.27 | 0.00 | 0.27 |
| Steam ($H_2O$) | 0.30 | 0.00 | 15.44 | 39.23 | 0.73 | 1.39 | 0.11 | 0.00 | 0.00 |
| Oxygen ($O_2$) | 16.72 | 0.00 | 0.08 | 0.00 | 0.08 | 0.00 | 0.08 | 0.00 | 0.08 |
| Acetic acid ($CH_3COOH$) | 0.00 | 0.00 | 3.05 | 3.05 | 0.00 | 0.00 | 0.00 | 0.00 | 0.00 |

TABLE 3-continued

Simulation results for oxygen separation module

|  | Case 0 | Case 1 | Case 2 | Case 3 |
|---|---|---|---|---|
| Methane ($CH_4$) | 0 | 0 | 0 | 0 |
| Oxygen ($O_2$) | 0 | 17.00 | 17.00 | 17.00 |
| Nitrogen ($N_2$) | 0 | 0 | 0 | 0 |
| Steam ($H_2O$) | 0 | 0 | 2.00 | 1.00 |

Results of the simulation show that under conditions where no methane is added via line 23 to overhead stream 16, there are not enough combustible C1 hydrocarbons present in the overhead stream 16 for raising the temperature within the oxygen separation module to above 850° C. The resulting temperature of 568° C. corresponded with no $O_2$ crossing, the membrane and ultimately leaving the oxygen separation module via line oxygen enriched bottom line 22. In Cases 1-3, the addition of methane at a flow rate of 2.1 kg/hr via line 23 was sufficient to raise the temperature of the module to 850° C. All three cases result in 17 kg/hr of $O_2$ leaving the module, which exceeds the amount of 16.7 kg/hr entering ODH reactor 1 in the earlier simulation. On a final note, it is not surprising that Cases 2 and 3 provided for carbon dioxide in oxygen enriched bottom line 22, as those cases included sending the overhead stream into the permeate side. Carbon dioxide is produced by combustion of the methane added to the permeate side. The carbon dioxide present in oxygen enriched bottom line 22 can act as inert diluent in the reaction in the ODH reactor 1.

What is claimed is:

1. A process for the oxidative dehydrogenation of a lower alkane into a corresponding alkene, the process comprising:
   i) contacting, in at least one oxidative dehydrogenation reactor, optionally in the presence of an inert diluent, an oxygen containing gas and a lower alkane containing gas, with an oxidative dehydrogenation catalyst to produce a product stream comprising the corresponding alkene, and one or more of:
      a. unreacted lower alkane;
      b. oxygen;
      c. inert diluent;
      d. carbon oxides, including carbon dioxide and carbon monoxide;
      e. oxygenates, including but not limited to, one or more of acetic acid, acrylic acid and maleic acid; and
      f. water;
   ii) passing the product stream from i) through a quench tower to remove oxygenates and water from the product stream;
   iii) passing the product stream from ii) through an amine wash to remove carbon dioxide from the product stream;
   iv) passing the product stream from iii) through a dryer to remove water;
   v) passing the product stream from iv) through a distillation tower to separate an overhead stream comprising C1 hydrocarbons and any other compounds lighter than C2/C2+ hydrocarbons;
   vi) passing the overhead stream from v) and optionally a combustible fuel into one or both of a retentate side and a permeate side of an oxygen separation module comprising an oxygen transport membrane;
   vii) introducing atmospheric air into the retentate side allowing for generation of heat by combustion of the overhead stream and the optional fuel within the retentate side to increase the temperature of the oxygen transport membrane to at least 850° C. permitting unreacted oxygen from the atmospheric air to cross the oxygen transport membrane into the permeate side producing an oxygen enriched gas on the permeate side and leaving an oxygen depleted air containing combustion products on the retentate side;
   viii) expelling the oxygen depleted air from the retentate side through an exhaust on the oxygen separation module; and
   x) removing the oxygen enriched gas through an oxygen rich outlet on the oxygen separation module;
   optionally, the oxygen enriched gas is directed back to i) as, or a portion of, the oxygen containing gas introduced into the oxidative dehydrogenation reactor.

2. The process of claim 1 wherein the oxygen enriched gas comprises at least 20% oxygen.

3. The process of claim 1 wherein the lower alkane is ethane.

4. The process of claim 1 wherein the ratio of lower alkane containing gas to oxygen containing gas is above the upper explosive limit.

5. The process of claim 1 wherein the lower alkane containing gas and the oxygen containing gas are mixed in a flooded gas mixer prior to entry into the at least one oxidative dehydrogenation reactor.

6. The process of claim 1 wherein the oxidative dehydrogenation catalyst comprises a mixed metal oxide selected from the group comprising:
   i) catalysts of the formula:

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;
   ii) catalysts of the formula:

wherein: g is a number from 0.1 to 0.9; h is a number from 0.04 to 0.9; i is a number from 0 to 0.5; j is a number from 0 to 0.5; and f is a number to satisfy the valence state of the catalyst; A is selected from the group consisting of Ti, Ta, V, Nb, Hf, W, Y, Zn, Zr, Si and Al or mixtures thereof; B is selected from the group consisting of La, Ce, Pr, Nd, Sm, Sb, Sn, Bi, Pb, TI, In, Te, Cr, Mn, Mo, Fe, Co, Cu, Ru, Rh, Pd, Pt, Ag, Cd, Os, Ir, Au, Hg, and mixtures thereof; D is selected from the group consisting of Ca, K, Mg, Li, Na, Sr, Ba, Cs, and Rb and mixtures thereof; and O is oxygen;
   iii) catalysts of the formula:

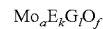

wherein: E is selected from the group consisting of Ba, Ca, Cr, Mn, Nb, Ta, Ti, Te, V, W and mixtures thereof; G is selected from the group consisting of Bi, Ce, Co, Cu, Fe, K, Mg, V, Ni, P, Pb, Sb, Si, Sn, Ti, U, and mixtures thereof; and when a=1, k is 0 to 2; l=0 to 2, with the proviso that the total value of 1 for Co, Ni, Fe and mixtures thereof is less than 0.5; and f is a number to satisfy the valence state of the catalyst;

iv catalysts of the formula:

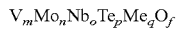

wherein: Me is a metal selected from the group consisting of Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; and when a=1.0; r=0.05 to 1.0; s=0.001 to 1.0; t=0.001 to 1.0; u=0.001 to 0.5; v=0.001 to 0.3; and f is a number to satisfy the valence state of the catalyst.

7. The process of claim 1 wherein one or more of the at least one oxidative dehydrogenation reactor comprises at least one reactor of a fixed bed type.

8. The process of claim 1 wherein one or more of the at least one oxidative dehydrogenation reactor comprises at least one reactor of a fluidized bed type.

9. The process of claim 1 wherein one or more of the at least one oxidative dehydrogenation reactor comprises at least one swing bed type reactor arrangement.

10. The process of claim 1 wherein the at least one oxidative dehydrogenation reactor comprises more than one oxidative dehydrogenation reactor, each comprising the same or different oxidative dehydrogenation catalyst, connected in series, and wherein the product stream from each oxidative dehydrogenation reactor except the last oxidative dehydrogenation reactor in the series is fed into a downstream oxidative dehydrogenation reactor; wherein at least one of the oxidative dehydrogenation reactors comprises a fixed bed type reactor, a fluidized bed type reactor or a swing bed type reactor arrangement.

11. The process of claim 1 wherein the at least one oxidative dehydrogenation reactor comprises more than one oxidative dehydrogenation reactor connected in parallel and each comprising the same or different dehydrogenation catalyst; wherein at least one of the oxidative dehydrogenation reactors comprises a fixed bed type reactor, a fluidized bed type reactor or a swing bed type reactor arrangement.

12. The process of claim 1 wherein the product stream from the at least one oxidative dehydrogenation reactor is passed through at least one heat exchanger immediately upstream of the quench tower to reduce temperature of the product stream.

13. The process of claim 1, further comprising a caustic wash tower immediately downstream of the amine wash.

14. The process of claim 1 wherein the oxygen enriched gas comprises at least 70% oxygen.

15. The process of claim 1 wherein the oxygen enriched gas comprises at least 80% oxygen.

* * * * *